United States Patent [19]

White, Jr. et al.

[11] Patent Number: 4,861,790

[45] Date of Patent: Aug. 29, 1989

[54] USE OF AZUMOLENE FOR THE TREATMENT OF MALIGNANT HYPERTHERMIA

[75] Inventors: Ralph L. White, Jr.; Keith O. Ellis, both of Norwich, N.Y.

[73] Assignee: Norwich Eaton Pharmaceuticals, Inc., Norwich, N.Y.

[21] Appl. No.: 114,462

[22] Filed: Oct. 28, 1987

[51] Int. Cl.$^4$ .............................................. A61K 31/42
[52] U.S. Cl. ....................................................... 514/374
[58] Field of Search ........................................... 514/374

[56] References Cited

U.S. PATENT DOCUMENTS

| | | | |
|---|---|---|---|
| 3,415,821 | 12/1968 | Davis et al. | 260/240 |
| 4,049,650 | 9/1977 | White, Jr. | 548/311 |
| 4,543,359 | 9/1985 | Ellis et al. | 514/390 |

OTHER PUBLICATIONS

Felice-Johnson, J., T. Sudds, G. Bennett, "Malignant Hyperthermia: Current Perspectives", *American Journal of Hospital Pharmacy*, vol. 38, No. 5, (May, 1981) pp. 646–651.
Physicians' Desk Reference, 42nd Ed., p. 1475 (1988).
Physicians' Desk Reference, 42nd Ed., p. 1476 (1988).

*Primary Examiner*—Jerome D. Goldberg
*Attorney, Agent, or Firm*—Milton B. Graff, IV; David L. Suter; Jack D. Schaeffer

[57] ABSTRACT

The invention involves a method for treating or preventing a malignant hyperthermia reaction in a human or lower animal by administering a safe and effective amount of azumolene.

10 Claims, No Drawings

USE OF AZUMOLENE FOR THE TREATMENT OF MALIGNANT HYPERTHERMIA

TECHNICAL FIELD

This invention is concerned with a method for the treatment of malignant hyperthermia. More particularly, it is concerned with the use of azumolene for the treatment of malignant hyperthermia.

BACKGROUND OF THE INVENTION

The incidence, etiology, clinical manifestations, and management of malignant hyperthermia (MH) are reviewed in Felice-Johnson, J., T. Sudds & G. Bennett, "Malignant Hyperthermia: Current Perspectives", *American Journal of Hospital Pharmacy*, Vol. 38, No. 5 (May, 1981), pp. 646-651. The syndrome of MH is recognized as one of the causes of anesthesia-related deaths. It is considered pharmacogenetic because both an abnormal gene and precipitating environmental factors are necessary to produce an acute MH reaction. Metabolic defects, involving a derangement of calcium dynamics, appear to be the common characteristic of susceptible individuals. Calcium release and uptake from the sarcoplasmic reticulum is altered when an individual with MH is exposed to certain anesthetic agents or triggering physical and emotional stresses. Muscle rigidity, tachycardia, tachypnea, and high fever can lead to other complications and death.

Management of an acute reaction of MH includes cooling methods to lower body temperature, hyperventilation, sodium bicarbonate control of acidosis, maintenance of fluid and electrolyte balance, and administration of dantrolene sodium. The early administration of dantrolene sodium in acute reaction of MH has been shown to rapidly alleviate the symptoms and ensuing severe complications.

Dantrolene sodium, 1-[[[5-(4-nitrophenyl)-2-furanyl]-methylene]amino]-2,4-imidazolidinedione sodium salt, is commercially available as a muscle relaxant drug and is also indicated for the treatment of malignant hyperthermia; see *Physicians Desk Reference*, 41st Edition (1987), E. R. Barnhardt (Pub.), Medical Economics Company, Inc., page 1412. The use of dantrolene sodium as a cardiac antiarrhythmic agent is disclosed in U.S. Pat. No. 4,543,359 issued to Ellis & Moore on Sept. 24, 1985.

Azumolene is 1-[[[5-(4-bromophenyl)-2-oxazolyl]methylene]amino]-2,4-imidazolidinedione. Azumolene is disclosed to be useful as a muscle relaxant in U.S. Pat. No. 4,049,650 issued to White on Sept. 20, 1977, the disclosure of which is hereby incorporated by reference. Example V of U.S. Pat. No. 4,049,650 discloses a method for preparing azumolene.

SUMMARY OF THE INVENTION

It is an object of the present invention to provide a method for the treatment of malignant hyperthermia.

The present invention involves the use of azumolene for the treatment of malignant hyperthermia.

DETAILED DESCRIPTION OF THE INVENTION

As used herein, "azumolene" means 1-[[[5-(4-bromophenyl)-2-oxazolyl]methylene]amino]-2,4-imidazolidinedione, of a pharmaceutically acceptable salt or hydrate thereof. A preferred form of azumolene for use in the treatment of malignant hyperthermia is the monosodium salt of azumolene. As used herein, "azumolene sodium" means the monosodium salt of azumolene or a hydrate thereof.

The present invention involves a method for the treatment of malignant hyperthermia (MH) in a human or lower animal by the administration of a safe and effective amount of azumolene. The present invention also involves a method for the prevention of MH in a human or lower animal susceptible of experiencing such by the administration of a safe and effective amount of azumolene. Specific compositions to be used in the methods of the present invention must, accordingly, be pharmaceutically acceptable. As used herein, a "pharmaceutically-acceptable" component is one which is suitable for use with humans or lower animals without undue adverse side effects (such as toxicity, irritation, and allergic response) commensurate with a reasonable benefit/risk ratio. Further, as used herein, the term "safe and effective amount" refers to the quantity of a component which is sufficient to yield a desired therapeutic response without undue adverse affects (such as toxicity, irritation, or allergic response) commensurate with a reasonable benefit/risk ratio when used in the manner of this invention. The specific "safe and effective amount" will, obviously, vary with such factors as the particular condition that is being treated, the physical condition of the patient, the nature of concurrent therapy (if any), and the specific formulations employed in the present invention. Specifically, the methods of the present invention, for the treatment and prevention of MH in a human or lower animal, comprise the step of administering to said subject a safe and effective amount of azumolene.

As used herein, a human or lower animal susceptible to MH is one having an abnormal gene making such human or lower animal susceptible to MH. An MH episode may occur when a susceptible human or lower animal experiences an environmental factor which can trigger the episode. The environmental factor most often responsible for triggering an episode of MH is administration of potent, fat-soluble inhalational anesthetics. MH episodes may also be triggered by certain depolarizing-type skeletal muscle relaxants, such as succinylcholine and decamethonium. Amide local anesthetics, including lidocaine, mepivacaine, bupivacaine, and prilocaine also may trigger MH episodes. In addition, other pharmacologic agents can aggravate MH reactions, especially those affecting the parasympathetic and sympathetic nervous systems. Also, patients with severe muscle defects may experience MH crises which are induced by physical or emotional stresses, such as sudden changes from hot or cold environments, strenuous exercise, mild infections, extensive muscle injury, or extreme emotional excitement, tension or apprehension.

Felice-Johnson, Sudds & Bennett, which is incorporated herein by reference, discloses several methods for determining whether a person has an abnormal gene making him susceptible to an MH reaction. Family history of MH reactions, abnormal serum creatine phosphokinase level, in vitro halothane/caffeine-induced contracture tests performed on a muscle biopsy specimen, and ultramicroscopic examination of a muscle biopsy specimen to reveal abnormalities such as neurogenic atrophy, regeneration, fiber breakdown, and abnormal mitochondria, are methods for detecting MH susceptible patients.

The present invention involves the administration of azumolene for the treatment or prevention of a malignment hyperthermic reaction in a human or lower animal. A preferred dose of azumolene for treatment of an MH reaction is from about 0.5 mg azumolene/kg body weight to about 50 mg/kg; more preferred is a dose from about 5 mg/kg to about 30 mg/kg; most preferred is a dose of about 10 mg/kg. A preferred dose of azumolene for prevention of an MH reaction is from about 0.5 mg/kg to about 40 mg/kg; more preferred is a dose from about 1 mg/kg to about 30 mg/kg; most preferred is a dose from about 5 mg/kg to about 20 mg/kg.

The preferred method of administering azumolene for the treatment of a malignant hyperthermic reaction is parenteral intravenous administration, in order to achieve rapid reversal of the MH reaction. Other routes of administration which result in sufficient blood levels of azumolene to counteract the MH reaction may also be used. Such routes of administration include other parenteral routes of administration, oral administration, topical administration, etc.

The following nonlimiting example provides typical results of the treatment of MH with azumolene.

EXAMPLE

Ten pigs, male or female (25–70 kg.) and at least four months of age, are derived from a purebred litter of Pietran pigs which are genetically afflicted with MH susceptibility.

The animals are initially anesthetized and maintained with sodium thiopental 25 mg/kg intravenously; the trachea is intubated with a cuffed tube. The animals are ventilated with 100% oxygen delivered by a constant volume respirator delivering 10 ml/kg at rates averaging 14 respirations/min. In order to maintain normal arterial blood gas during control. The carotid artery is cannulated for the measurement of blood pressure and arterial blood sampling. A bipolar electrode catheter is advanced through the jugular vein and is used for monitoring right atrial electrograms and administration of drugs. An esophageal probe is used to monitor core temperature. Blood pressure and R—R interval are continuously displayed and recorded on an ink jet recorder (Siemens model 804) and stored on a Honeywell tape recorder (model 101). At intervals of five minutes, samples of arterial blood are taken for determination of pH and partial pressures of carbon dioxide and oxygen using a Corning blood gas analyzer (model 165/2). A sample of vastus lateralis muscle is also taken from six of the animals for caffeine contracture testing.

Following surgical preparation, the animals are allowed to equilibrate for a period of approximately 30 minutes followed by control readings of stated parameters. Halothane of 1% is then delivered by a vaporiser (Fluotec Mark 2) and succinylcholine (1 mg/kg) is given following control period.

The time to reach the MH reaction end point prior to treatment with azumolene sodium is defined by a combination of acidosis, rigidity, rising temperature, and hypercapnea.

The development of the MH reaction follows a very similar course in each animal. As the MH reaction develops, R—R interval reduction, blood pH reduction, blood partial pressure of carbon dioxide elevation, blood partial pressure of oxygen reduction, temperature elevation, and skeletal muscle rigidity are observed. The caffeine contracture test performed on six of the ten MH pigs is positive in all pigs.

Following treatment with azumolene sodium at a concentration of 10 mg/kg i.v., improvements in R—R interval, temperature, blood pH and partial pressures of carbon dioxide and oxygen, and relaxation of skeletal muscles occurred, resulted in a return to pre-MH inducement values for all the measured and observed parameters.

While particular embodiments of the present invention have been described, it will be obvious to those skilled in the art that various changes and modifications of the present invention can be made without departing from the spirit and scope of the invention. It is intended to cover, in the appended claims, all such modifications which are within the scope of this invention.

What is claimed is:

1. A method for treatment of a malignant hyperthermic reaction, comprising administering, to a human or lower animal subject in need of said treatment, an amount of azumolene that is safe and effective for treatment of said malignant hyperthermic reaction.

2. The method of claim 1 wherein said azumolene is azumolene sodium.

3. The method of claim 2 wherein said azumolene sodium is administered intravenously in an amount of from about 5 mg/kg to about 30 mg/kg.

4. The method of claim 3 wherein said subject is a human.

5. The method of claim 4 wherein said azumolene sodium is administered in an amount of about 10 mg/kg.

6. A method for the prevention of a malignant hyperthermic reaction comprising administering, to a human or lower animal subject having an abnormal gene making said subject susceptible to said reaction, an amount of azumolene that is safe and effective for prevention of said malignant hyperthermic reaction.

7. The method of claim 6 wherein said azumolene is azumolene sodium.

8. The method of claim 7 wherein said azumolene sodium is administered intravenously in an amount of from about 1 mg/kg to about 30 mg/kg.

9. The method of claim 8 wherein said subject is a human.

10. The method of claim 9 wherein said azumolene sodium is administered in an amount of from about 5 mg/kg to about 20 mg/kg.

* * * * *